(12) United States Patent
Kim et al.

(10) Patent No.: US 11,013,442 B2
(45) Date of Patent: May 25, 2021

(54) NEURAL ELECTRODE FOR MEASURING NEURAL SIGNAL AND METHOD FOR MANUFACTURING THE SAME

(71) Applicant: ELECTRONICS AND TELECOMMUNICATIONS RESEARCH INSTITUTE, Daejeon (KR)

(72) Inventors: Yong Hee Kim, Daejeon (KR); Sang-Don Jung, Daejeon (KR); Gook Hwa Kim, Daejeon (KR); Ah Young Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 1478 days.

(21) Appl. No.: 15/065,755

(22) Filed: Mar. 9, 2016

(65) Prior Publication Data

US 2016/0270680 A1    Sep. 22, 2016

(30) Foreign Application Priority Data

Mar. 19, 2015    (KR) .................. 10-2015-0038002

(51) Int. Cl.
*A61B 5/24* (2021.01)
*A61B 5/25* (2021.01)
(Continued)

(52) U.S. Cl.
CPC .................. *A61B 5/24* (2021.01); *A61B 5/25* (2021.01); *A61B 5/685* (2013.01); *A61B 5/6868* (2013.01);
(Continued)

(58) Field of Classification Search
CPC ........ A61B 5/04001; A61B 2562/0285; A61B 2562/125; A61B 5/04002; A61B 5/6848;
(Continued)

(56) References Cited

U.S. PATENT DOCUMENTS 4,468,420 A * 8/1984 Kawahara ............... C03C 17/25
106/287.34
6,896,780 B2   5/2005 Yang et al.
(Continued)

FOREIGN PATENT DOCUMENTS

JP    2009-0501600 A    1/2009
KR    10-2010-0058220 A    6/2010
(Continued)

OTHER PUBLICATIONS

A Basu, et al. "Enhancement of Transmittance of Indium Tin Oxide Coated Glass Plates," Indian J. of Pure & Applied Physics v. 48, Dec. 2010; pp. 899-903 (2010) (Year: 2010).*
(Continued)

*Primary Examiner* — Eun Hwa Kim

(57) ABSTRACT

Disclosed are a neural electrode for measuring a neural signal and a method for manufacturing the same. In the method, an indium tin oxide (ITO) electrode is formed on a substrate, an insulative passivation layer is formed on the substrate and the ITO electrode to expose a portion of the ITO electrode, and ITO nanorods are formed on the portion of the ITO electrode and the insulative passivation layer. Accordingly, it is possible to reduce electrical noise and improve a neurotrophic property by using the existing process.

2 Claims, 5 Drawing Sheets

(51) Int. Cl.
*A61N 1/05* (2006.01)
*C23C 14/08* (2006.01)
*A61B 5/00* (2006.01)

(52) U.S. Cl.
CPC ......... *A61N 1/0529* (2013.01); *A61N 1/0531* (2013.01); *C23C 14/086* (2013.01); *A61B 2562/0285* (2013.01); *A61B 2562/125* (2013.01)

(58) Field of Classification Search
CPC ..... A61B 5/685; A61B 5/6868; A61B 5/6877; C23C 14/086; A61N 1/0529–0536; A61N 1/0551–0556; A61N 1/0531
See application file for complete search history.

(56) References Cited

U.S. PATENT DOCUMENTS

| | | | | |
|---|---|---|---|---|
| 7,905,013 | B2* | 3/2011 | Zhang | A61N 1/0543 29/852 |
| 2003/0088166 | A1* | 5/2003 | Say | A61B 5/01 600/345 |
| 2007/0060815 | A1* | 3/2007 | Martin | A61B 5/0408 600/372 |
| 2008/0176271 | A1* | 7/2008 | Silver | A61B 5/6882 435/29 |
| 2010/0108132 | A1* | 5/2010 | Tsakalakos | H01L 21/02653 136/256 |
| 2010/0127206 | A1 | 5/2010 | Choi et al. | |
| 2011/0082413 | A1* | 4/2011 | Ready | A61N 1/05 604/20 |
| 2011/0087126 | A1* | 4/2011 | Zorzos | A61B 5/0478 600/544 |
| 2013/0030275 | A1* | 1/2013 | Seymour | A61N 5/0622 600/377 |
| 2014/0020936 | A1 | 1/2014 | Kim et al. | |

FOREIGN PATENT DOCUMENTS

| | | |
|---|---|---|
| KR | 10-2012-0052634 A | 5/2012 |
| KR | 10-2012-0054976 A | 5/2012 |
| KR | 10-2012-0061387 A | 6/2012 |
| WO | WO 2007/010441 A2 | 1/2007 |

OTHER PUBLICATIONS

JH Park, et al. "Wafer-Scale Growth of ITO Nanorods by Radio Frequency Magnetron Sputtering Deposition" 2011 J. Electrochem. Soc. 158 pp. K131-K135 (2011). (Year: 2011).*

Jae Hyoung Park et al., "Wafer-Scale Growth of ITO Nanorods by Radio Frequency Magnetron Sputtering Desposition", Journal of the Electrochemical Society, Mar. 21, 2011, pp. K131-K135, vol. 158, No. 5.

Muhammed K. Gheith et al., "Single-Walled Carbon Nanotube Polyelectrolyte Multilayers and Freestanding Films as a Biocompatible Platform for Neuroprosthetic Implants", Advanced Materials, 2005, pp. 2663-2670, vol. 17, Wiley-VCH Verlag GmbH & Co. KGaA.

* cited by examiner

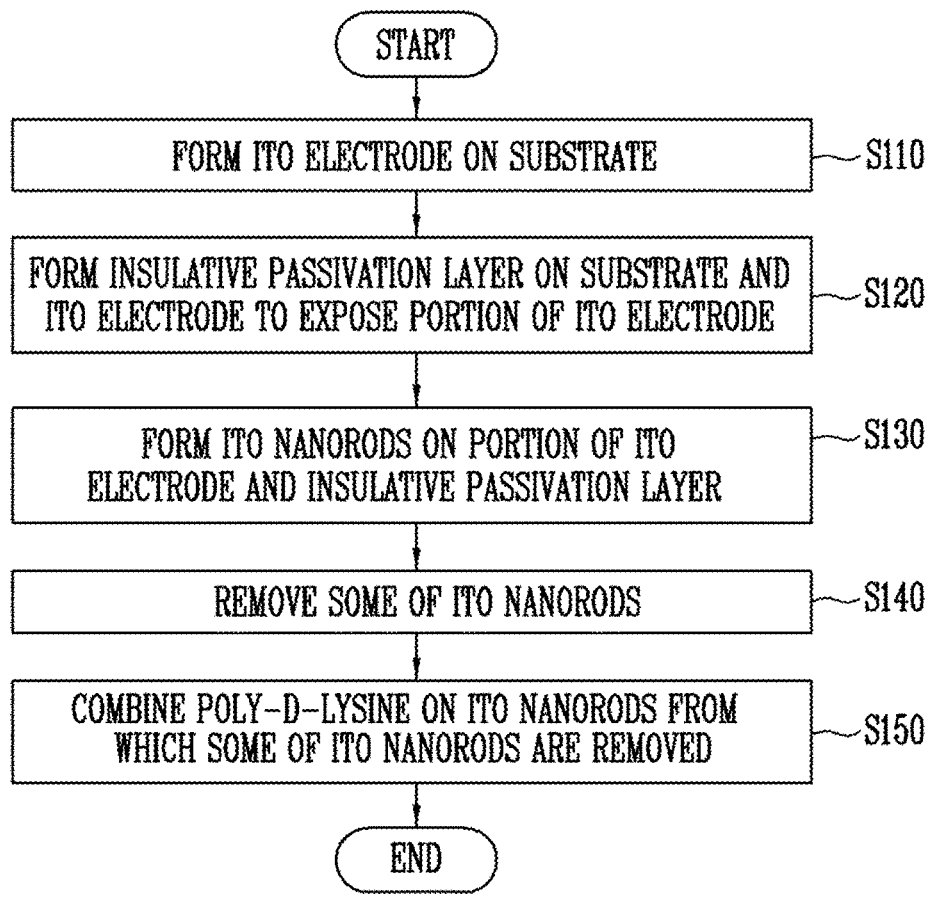
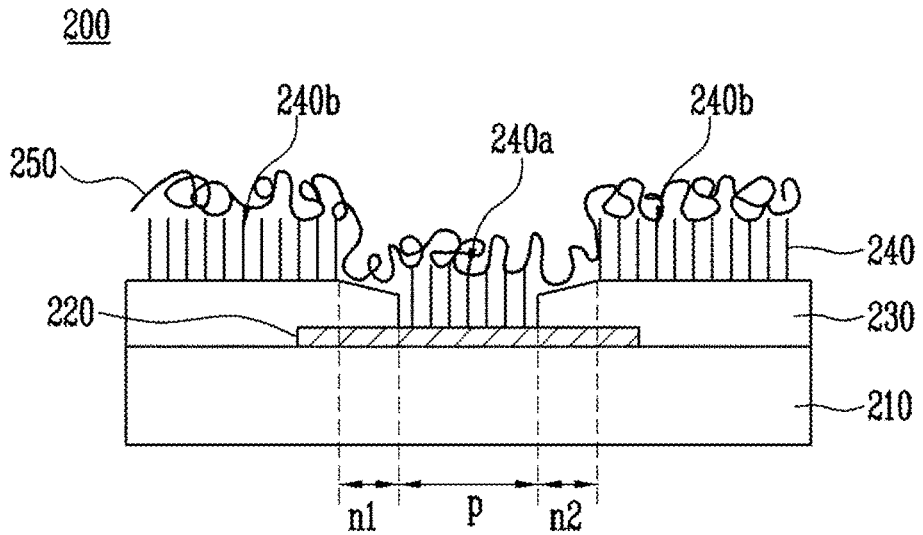

NEURAL ELECTRODE FOR MEASURING NEURAL SIGNAL AND METHOD FOR MANUFACTURING THE SAME

CROSS-REFERENCE TO RELATED APPLICATION

This application claims priority to and the benefit of Korean Patent Application No. 10-2015-0038002, filed on Mar. 19, 2015, in the Korean Intellectual Property Office, the entire contents of which are incorporated herein by reference in their entirety.

BACKGROUND

1. Field

An aspect of the present disclosure relates to a neural electrode for measuring a neural signal and a method for manufacturing the same.

2. Description of the Related Art

Studies on the development of materials for improving the performance of neural electrodes have conducted in in vivo or in vitro neural interface fields for recording neural signals from nerve cells.

As for the neural electrodes, a first-generation electrode made of metal wires such as white gold, gold, tungsten and iridium and a second-generation electrode including a semiconductor and a multi-electrode array were employed, and a third-generation electrode surface-modified as a nanostructure has been researched and developed.

To more accurately identify a nervous condition, it is necessary to record neural signals for each nerve cell. To this end, the size of neural electrodes is decreasing to that (about 10 μm) of the nerve cells.

In order to maintain valid signal measurement sensitivity even when the size of a neural electrode is small, the surface area per unit area of the electrode should be large. To this end, surface modification using a nanomaterial, etc. is being attempted.

An increase in the surface area of the electrode can reduce thermal noise and eventually improve signal-to-noise ratio (SNR).

Meanwhile, it is very important that neural electrodes are neurotrophic with nerve cells, and therefore, it is also very important that, in addition to the neurotrophic property of the neural electrodes, passivation materials of the neural electrodes are neurotrophic with the nerve cells.

SUMMARY

Embodiments provide a neural electrode for measuring a neural signal and a method for manufacturing the same, which can reduce electrical noise and improve a neurotrophic property by using the existing process.

These and other objectives of the present disclosure can be derived by those skilled in the art from the embodiments described below.

According to an aspect of the present disclosure, there is provided a method for manufacturing a neural electrode for measuring a neural signal, the method including: forming an indium tin oxide (ITO) electrode on a substrate; forming an insulative passivation layer on the substrate and the ITO electrode to expose a portion of the ITO electrode; and forming ITO nanorods on the portion of the ITO electrode and the insulative passivation layer.

The method may further include removing some of the ITO nanorods.

In the removing of the some of the ITO nanorods, ITO nanorods adjacent to an edge of the portion of the ITO electrode among the ITO nanorods may be removed.

The ITO nanorods adjacent to the edge of the portion of the ITO electrode may be positioned on the insulative passivation layer formed on the ITO electrode.

The ITO nanorods may include first nanorods formed on the portion of the ITO electrode and second nanorods on the insulative passivation layer. In the removing of the some of the ITO nanorods, ITO nanorods adjacent to the first nanorods among the second nanorods may be removed.

The removing of the some of the ITO nanorods may include: coating a photoresist on the ITO nanorods; patterning the photoresist to expose ITO nanorods adjacent to an edge of the portion of the ITO electrode; removing the exposed ITO nanorods; and removing the photoresist.

In the removing of the exposed ITO nanorods, an ITO echant may be used.

The method may further include combining poly-D-lysine on the ITO nanorods from which the some of the ITO nanorods are removed.

The forming of the ITO nanorods may be performed using sputtering or pulsed laser deposition.

According to an aspect of the present disclosure, there is provided a neural electrode for measuring a neural signal, including: a substrate; an ITO electrode formed on the substrate; an insulative passivation layer formed on the substrate and the ITO electrode, the insulative passivation layer exposing a portion of the ITO electrode; and ITO nanorods formed on the portion of the ITO electrode and the insulative passivation layer.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

FIG. 1 is a flowchart sequentially illustrating a method for manufacturing a neural electrode for measuring a neural signal according to an embodiment of the present disclosure.

FIG. 2 is a view schematically illustrating a neural electrode for measuring a neural signal, which is manufactured by the method according to the embodiment of the present disclosure.

DETAILED DESCRIPTION

Figure 3A:
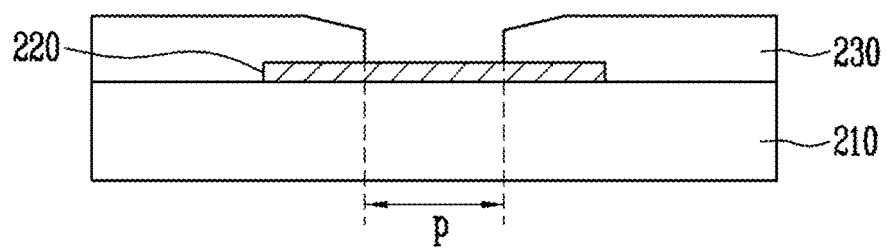
FIGS. 3A to 3E are views schematically illustrating steps in the method according to the embodiment of the present disclosure.

The specific structural or functional description disclosed herein is merely illustrative for the purpose of describing embodiments according to the concept of the present disclosure. The embodiments according to the concept of the present disclosure can be implemented in various forms, and cannot be construed as limited to the embodiments set forth herein. Throughout the drawings, like elements are designated by like reference numerals.

Hereinafter, exemplary embodiments of the present disclosure will be described in detail with reference to the accompanying drawings.

FIG. 1 is a flowchart sequentially illustrating a method for manufacturing a neural electrode for measuring a neural signal according to an embodiment of the present disclosure.

FIG. 2 is a view schematically illustrating a neural electrode 200 for measuring a neural signal, which is manufactured by the method according to the embodiment of the present disclosure.

As shown in FIG. 1, the method for manufacturing a neural electrode for measuring a neural signal (hereinafter, for convenience of illustration, referred to as the 'neural electrode manufacturing method') according to the embodiment of the present disclosure may include a step of forming an indium tin oxide (ITO) electrode (S110), a step of forming an insulative passivation layer (S120), a step of forming ITO nanorods (S130), a step of removing some of the ITO nanorods (S140), and a step of combining poly-D-lysine (S150).

In addition, as shown in FIG. 2, the neural electrode 200 for measuring a neural signal, manufactured by the neural electrode manufacturing method (hereinafter, for convenience of illustration, referred to as the 'neural electrode') according to the embodiment of the present disclosure may include a substrate 210, an ITO electrode 220, an insulative passivation layer 230, ITO nanorods 240, and poly-D-lysine 250.

According to the embodiment of the present disclosure, the ITO electrode is formed on the substrate 210, and the insulative passivation layer 230 is formed on the substrate and the ITO electrode 220 to expose a portion p of an upper of the ITO electrode 220. The ITO nanorods 240 are formed on the portion p of the ITO electrode and the insulative passivation layer 230.

In this case, the ITO nanorods 240 may be divided into first nanorods 240a formed on the portion p of the ITO electrode 220 and second nanorods 240b formed on the insulative passivation layer 230. The first nanorods 240a and the second nanorods 240b may be spaced apart from each other by regions n1 and n2 in which the ITO nanorods do not exist.

The regions n1 and n2 in which the ITO nanorods do not exist may be positioned on the insulative passivation layer 230 formed on the ITO electrode 220. That is, the regions n1 and n2 may exist on a position at which both the ITO electrode 220 and the insulative passivation layer 230 exist.

In addition, the poly-D-lysine 250 is combined on the ITO nanorods 240.

A nanostructure refers to a structure of which length, thickness, or diameter is a few thousand of nanometers, and may be a thin film, a nanotube, a nanorod, a nanosphere, or another arbitrary shape. However, according to an embodiment of the present disclosure, nanorods are formed on an ITO electrode including a passivation layer.

ITO is widely used as a transparent conductor in displays, solar cells, touch panels, and the like. In addition, the ITO is used in connection of a neural electrode and an input/output pad. Since the ITO is transparent and conductive, the ITO not only facilitates the observation of nerve cells but also facilitates the chemical fixation of neurotrophic neural adhesive molecules to nerve cells.

However, like gold, an ITO neural electrode has a large impedance, and hence thermal noise is large. Therefore, the ITO neural electrode is not widely used due to inadequacy in the observation of neural signals. The impedance of an electrode is closely related to electrical noise, and the electrical noise may be reduced as the impedance of the electrode decreases. In addition, the impedance of the electrode decreases as the surface area of the electrode increases. Hence, as the surface area of the electrode increases, electrical characteristics of the electrode can be improved.

Meanwhile, it is reported that nerve cells are better grown on a rough surface in a nano-scale, as compared with a flat substrate.

According to the present disclosure, it is possible to reduce electrical noise and improve a neurotrophic property by using the existing process. Thus, the neural electrode manufacturing method according to the embodiment of the present disclosure will be described in detail with reference to FIGS. 3 to 5C in conjunction with FIGS. 1 and 2.

FIGS. 3A to 3E are views schematically illustrating the steps in the neural electrode manufacturing method according to the embodiment of the present disclosure.

Figure 4:
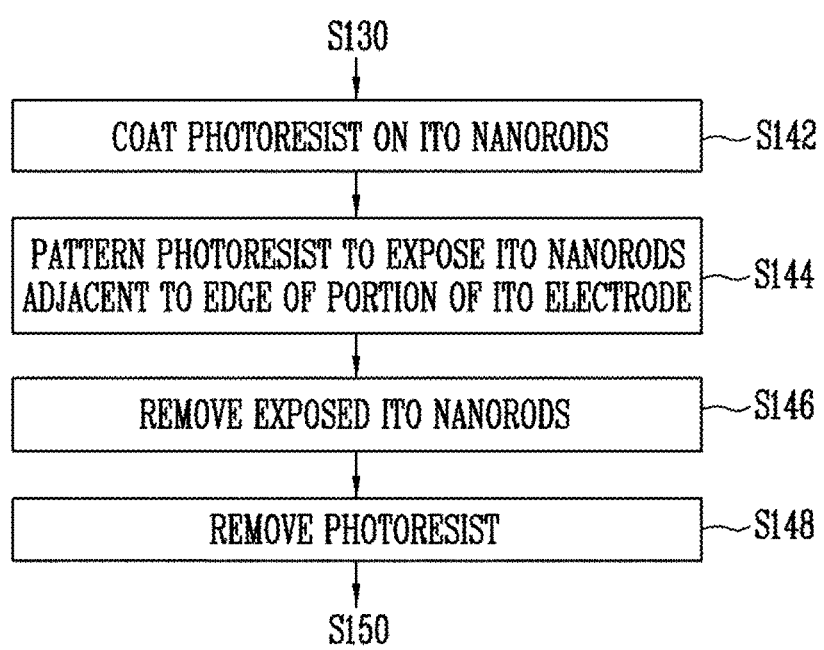
FIG. 4 is a flowchart sequentially illustrating in detail a step of removing some of indium tin oxide (ITO) nanorods in the method according to the embodiment of the present disclosure.

FIG. 4 is a flowchart sequentially illustrating in detail the step of removing the some of the ITO nanorods (S140) in the neural electrode manufacturing method according to the embodiment of the present disclosure.

Figure 5A:
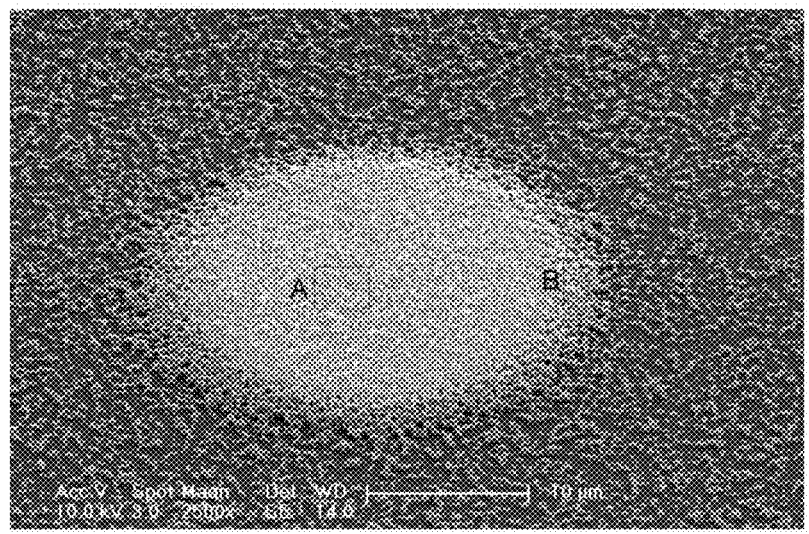
FIG. 5A is a scanning electron microscope (SEM) image of ITO nanorods coated on an ITO electrode through a pulse laser deposition technique according to the embodiment of the present disclosure.
Figure 5B:
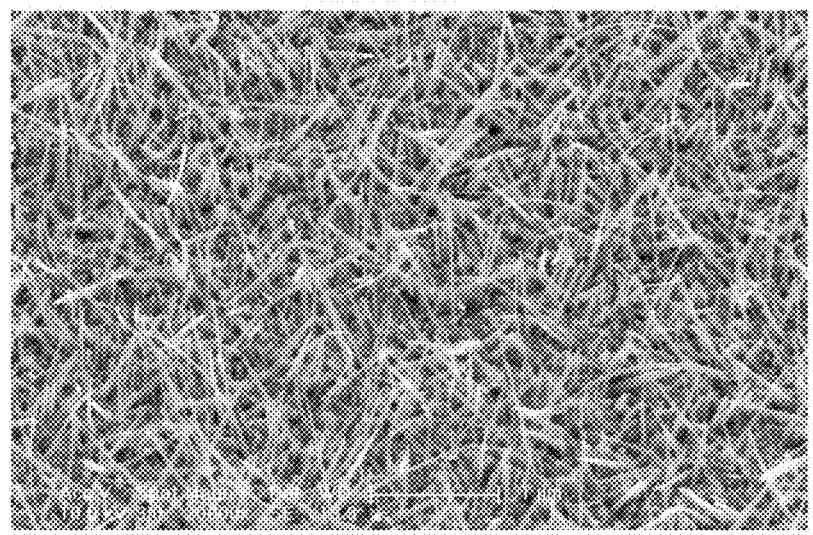
FIG. 5B is an enlarged view of area A of FIG. 5A for illustrating in detail the ITO nanorods coated on the ITO electrode.
Figure 5C:
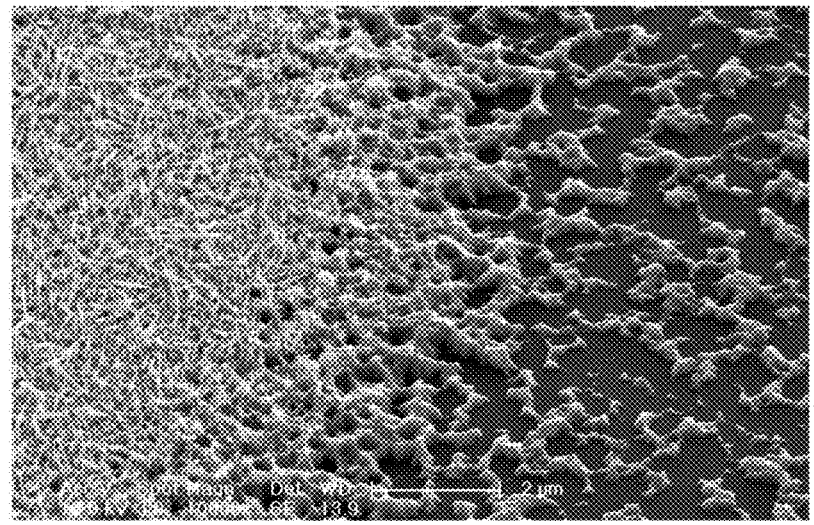
FIG. 5C is an enlarged view of area B of FIG. 5A for illustrating in detail partially etched ITO nanorods.

FIG. 5A is a scanning electron microscope (SEM) image of ITO nanorods coated on an ITO electrode through a pulse laser deposition technique according to the embodiment of the present disclosure. FIG. 5B is an enlarged view of area A of FIG. 5A for illustrating in detail the ITO nanorods coated on the ITO electrode. FIG. 5C is an enlarged view of area B of FIG. 5A for illustrating in detail partially etched ITO nanorods.

First, as shown in FIGS. 1 and 3A, in steps S110 and S120, an ITO electrode 220 is formed on a substrate 210, and an insulative passivation layer 230 is formed on the substrate 210 and the ITO electrode 220 to expose a portion p of the ITO electrode 220. That is, in steps S110 and S120, an ITO electrode including a passivation layer (hereinafter, for convenience of illustration, referred to as a 'passivation layer ITO electrode') is formed.

The substrate 210 may be an ITO substrate or a substrate made of an inorganic material such as glass, silicon, or quartz. The ITO electrode 220 may be formed by depositing ITO on the substrate 210 and patterning the deposited ITO.

The insulative passivation layer 230 may be made of silicon oxide.

Figure 3B:
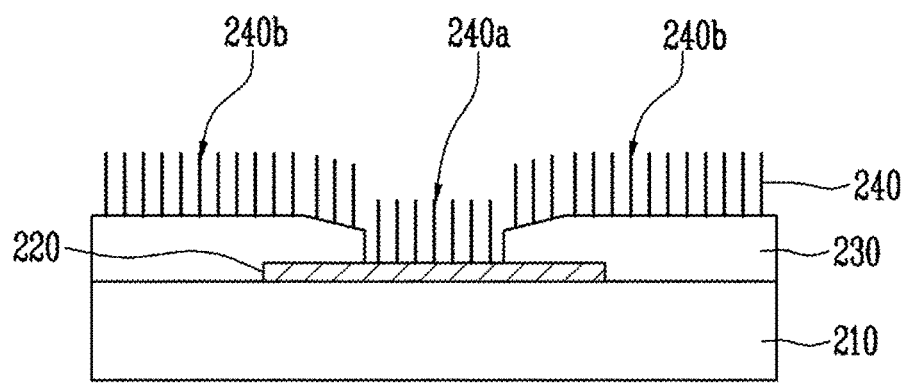
Figure 3C:
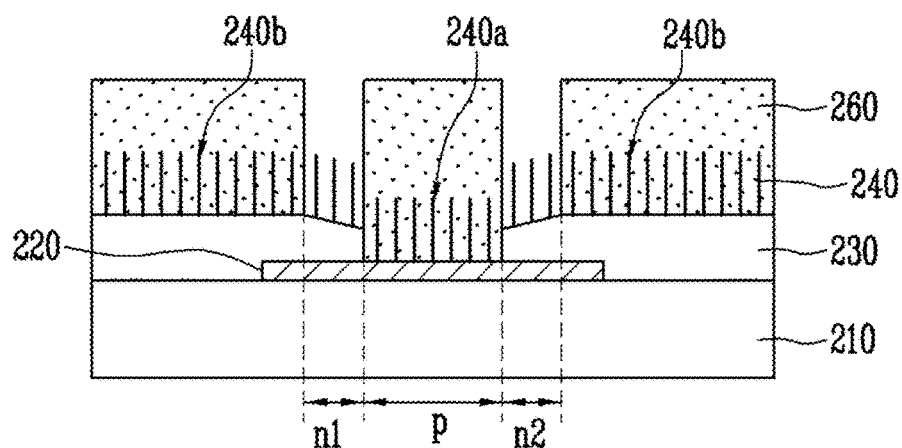
Figure 3D:
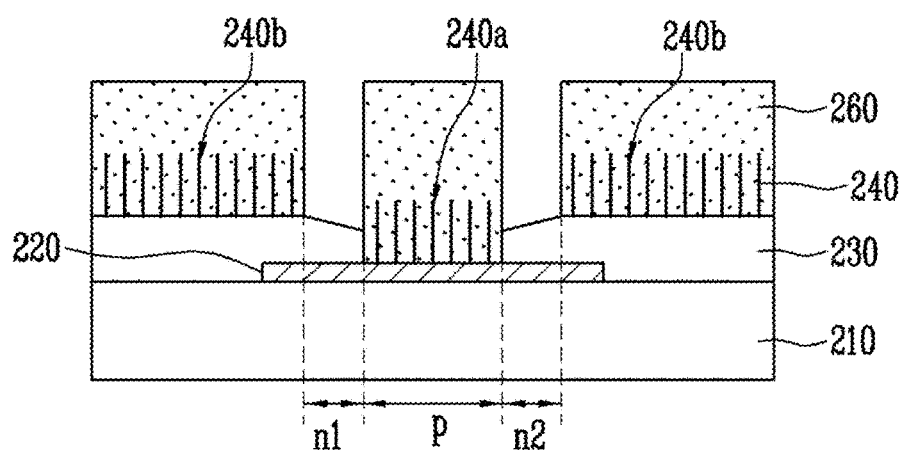
Figure 3E:
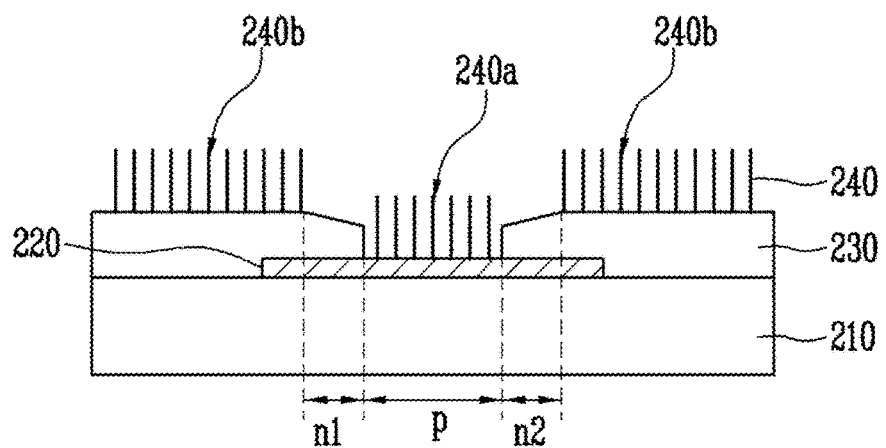

Next, as shown in FIGS. 1 and 3B, in step S130, ITO nanorods 240 are formed on the portion p of the ITO electrode 220 and the insulative passivation layer 230. That is, in step S130, the ITO nanorods 240 are formed on the passivation layer ITO electrode formed in steps S110 and S120.

According to an embodiment of the present disclosure, in step S130, the ITO nanorods 240 having a length of a few µm may be formed on the passivation layer ITO electrode by using sputtering or pulsed laser deposition (PLD). The sputtering is a kind of vacuum deposition and refers to a method of forming a layer on a substrate, by generating plasma under a relatively low level of vacuum to accelerate gas such as ionized argon and applying the plasma onto a target such that desired atoms are discharged from the target. The PLD refers to a method in which a ceramic target to be made is positioned in a vacuum chamber, and plasma bounced by irradiating pulse laser focused with a lens onto the target is crystallized on a substrate opposite to the target.

The ITO nanorods 240 formed on the passivation layer ITO electrode may be divided into first nanorods 240a formed on the portion p of the ITO electrode 220 and second nanorods 240b formed on the insulative passivation layer 230.

Continuously, as shown in FIGS. 1, 3C to 3E, in step S140, the some of the ITO nanorods 240 formed on the passivation layer ITO electrode are removed.

More specifically, in step S140, ITO nanorods adjacent to an edge of the portion p of the ITO electrode 220 among the ITO nanorods 240 formed on the passivation layer ITO electrode may be removed.

Since the ITO nanorods 240 formed on the passivation layer ITO electrode, as described above, may be divided into the first nanorods 240a formed on the portion p of the ITO electrode 220 and the second nanorods 240b formed on the insulative passivation layer 230, in step S140, ITO nanorods adjacent to the first nanorods 240a among the second nanorods 240b may be removed.

Accordingly, the first nanorods 240a and the second nanorods 240b may be spaced apart from each other by regions n1 and n2 in which the ITO nanorods do not exist, so that the ITO electrode 220 and the other portion are electrically isolated from each other, thereby improving the signal-to-noise ratio (SNR) of the ITO electrode 220.

To this end, as shown in FIG. 4, after step S130, a step of coating a photoresist 260 on the ITO nanorods 240 formed on the passivation layer ITO electrode (S142), a step of patterning the photoresist 260 to expose ITO nanorods adjacent to an edge of the portion p of the ITO electrode 220 (S144), a step of removing the exposed ITO nanorods (S146), and a step of removing the photoresist 260 (S148) may be performed.

Here, the ITO nanorods adjacent to the edge of the portion p of the ITO electrode 220, i.e., the exposed nanorods are positioned on the insulative passivation layer 230 formed on the ITO electrode 220. In other words, the ITO nanorods adjacent to the first nanorods 240a among the second nanorods 240b are positioned on the insulative passivation layer 230 formed on the ITO electrode 220, and are removed in step S146.

In order to remove the exposed ITO nanorods in step S146, an ITO echant may be used.

In order to remove the photoresist 260 in step S148, a solvent such as acetone may be used.

Finally, as shown in FIGS. 1 and 2, in step S150, poly-D-lysine is combined on the ITO nanorods 240 on which the steps from step S110 to step S148 are completely performed.

According to an embodiment of the present disclosure, in step S150, molecules such as poly-D-lysine may be fixed on the entire area including ITO nanostructures by performing treatment of a strong acid such as a nitric acid or oxygen plasma and then floating positive ions using a self-assembled monolayer.

Here, the poly-D-lysine has a high coherence with nerve cells. According to the present disclosure, it is possible to enhance the neural signal measurement performance of the neural electrode and improve neurotrophic and biotrophic properties.

According to the present disclosure, it is possible to reduce electrical noise and improve a neurotrophic property by using the existing process.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present disclosure as set forth in the following claims.

What is claimed is:

1. A neural electrode for measuring a neural signal, comprising:
a substrate;
an indium tin oxide (ITO) electrode disposed on the substrate;
an insulative passivation layer disposed on the substrate and the ITO electrode, the insulative passivation layer exposing a portion of the ITO electrode;
first ITO nanorods disposed on the ITO electrode; and
second ITO nanorods disposed on the insulative passivation layer,
wherein the first and second ITO nanorods are separated from one another by a portion in which the first and second ITO nanorods do not exist,
wherein the region in which the first and second ITO nanorods do not exist is positioned on the insulative passivation layer formed on the ITO electrode, and
wherein the neural electrode further comprises poly-D-lysine disposed over the first and second ITO nanorods and extending over the portion in which the first and second ITO nanorods do not exist.

2. The neural electrode of claim 1, wherein edges of the ITO electrode are covered by the passivation layer.

* * * * *